(12) United States Patent
Chilese et al.

(10) Patent No.: US 9,164,388 B2
(45) Date of Patent: Oct. 20, 2015

(54) TEMPERATURE CONTROL IN EUV RETICLE INSPECTION TOOL

(71) Applicants: Frank Chilese, San Ramon, CA (US);
Daniel Wack, Fredricksburg, VA (US);
Douglas Fowler, San Jose, CA (US)

(72) Inventors: Frank Chilese, San Ramon, CA (US);
Daniel Wack, Fredricksburg, VA (US);
Douglas Fowler, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 287 days.

(21) Appl. No.: 13/857,278

(22) Filed: Apr. 5, 2013

(65) Prior Publication Data
US 2013/0265557 A1    Oct. 10, 2013

Related U.S. Application Data

(60) Provisional application No. 61/622,309, filed on Apr. 10, 2012, provisional application No. 61/794,451, filed on Mar. 15, 2013.

(51) Int. Cl.
*G03B 27/32* (2006.01)
*G03B 27/42* (2006.01)
*G03F 7/20* (2006.01)
*G03F 1/84* (2012.01)
*G03F 1/22* (2012.01)

(52) U.S. Cl.
CPC .. *G03F 7/20* (2013.01); *G03F 1/84* (2013.01); *G03F 7/70875* (2013.01); *G03F 1/22* (2013.01)

(58) Field of Classification Search
CPC .............................. G03F 7/20; G03F 7/70875
USPC ............................ 355/30, 53, 75; 250/492.2
See application file for complete search history.

(56) References Cited

U.S. PATENT DOCUMENTS

| | | | |
|---|---|---|---|
| 6,359,678 B1 * | 3/2002 | Ota | 355/53 |
| 6,445,439 B1 * | 9/2002 | McCullough | 355/30 |
| 7,323,698 B2 * | 1/2008 | Sogard | 250/492.2 |
| 7,359,029 B2 * | 4/2008 | Finders et al. | 355/30 |
| 7,599,545 B2 | 10/2009 | Shibata et al. | |
| 7,921,803 B2 | 4/2011 | Yudovsky et al. | |

(Continued)

FOREIGN PATENT DOCUMENTS

JP      2006173245 A    6/2006

OTHER PUBLICATIONS

International Search Report and Written Opinion mailed Jul. 5 2013, in PCT/US2013/035667.

(Continued)

*Primary Examiner* — Hung Henry Nguyen
(74) *Attorney, Agent, or Firm* — Joshua D. Isenberg; JDI Patent

(57) ABSTRACT

An apparatus comprises an optics assembly and a plate. The optics assembly configured to focus light from an EUV source onto a reticle or sensor. The plate has an opening to allow the EUV light to pass through disposed between the optics assembly and the reticle or sensor. The plate is cooled to a temperature less than that of the reticle or sensor. The plate is engineered to balance out heat absorbed from the reticle or sensor with heat absorbed by the plate. It is emphasized that this abstract is provided to comply with the rules requiring an abstract that will allow a searcher or other reader to quickly ascertain the subject matter of the technical disclosure. It is submitted with the understanding that it will not be used to interpret or limit the scope or meaning of the claims.

20 Claims, 5 Drawing Sheets

(56) References Cited

U.S. PATENT DOCUMENTS

| | | |
|---|---|---|
| 8,102,522 B2 | 1/2012 | Suga et al. |
| 2002/0034834 A1 | 3/2002 | Verdiell |
| 2003/0151130 A1 | 8/2003 | Cheon |
| 2004/0051984 A1 | 3/2004 | Oshino et al. |
| 2004/0079518 A1 | 4/2004 | del Puerto et al. |
| 2004/0256574 A1* | 12/2004 | Namba .................. 250/492.1 |
| 2005/0110967 A1* | 5/2005 | Hara et al. ................. 355/30 |
| 2010/0259734 A1 | 10/2010 | Knarren et al. |
| 2011/0024623 A1 | 2/2011 | Hatakeyama et al. |

OTHER PUBLICATIONS

U.S. Appl. No. 61/622,309, filed Apr. 10, 2012.
U.S. Appl. No. 61/794,451, filed Mar. 15, 2013.

* cited by examiner

TEMPERATURE CONTROL IN EUV RETICLE INSPECTION TOOL

CLAIM PRIORITY

This application is related to commonly owned, U.S. Provisional Patent Application No. 61/622,309, filed Apr. 10, 2012, and U.S. Provisional Patent Application No. 61/794,451, filed Mar. 15, 2013, the entire contents of which are incorporated herein by reference.

FIELD OF THE INVENTION

Aspects of the present disclosure relate to extreme ultraviolet (EUV) processes. More specifically, aspects of the present disclosure relate to temperature control of a reticle and sensitive optics in EUV inspection and lithography tools.

BACKGROUND OF THE INVENTION

The optics assemblies in extreme ultraviolet (EUV) tools are very sensitive to temperature changes. The optics are generally assembled and tested at a specific temperature (normally around 22° C.) and anything that outside elements do to change the temperature of portions of the optics assembly can degrade the performance of the optics, and thus, the entire tool. However, when EUV light strikes a reticle or a target, it is partially absorbed at the surface. This creates a spot on the reticle or target which has an elevated temperature. This spot will radiate that heat to nearby objects, including the illumination optics and the imaging optics in the optics assemblies. In general, this heated spot will be higher in temperature than any nearby hardware.

Thermal control in this region of a reticle inspection tool has not been required in the past because the thermal control of prior optical delivery assemblies has not been as demanding. In addition, prior art devices utilized particle protection devices, e.g., a pellicle, which also acted as a radiation barrier, absorbing heat from the reticle and reradiating it away in a less direct manner. However inspection and lithography tools that use extreme ultraviolet (EUV) light may not be able to use a pellicle because the pellicle might absorb a potentially unacceptable amount of EUV light.

Prior methods have generally not required a radiative offset to the heat load from the hot spot on the reticle. This has been due to: a) the hot spot being cooler due to higher reflectivity of the reticle to wavelengths longer than EUV, b) the radiation attenuating characteristics of the pellicle, c) the reduced thermal sensitivity of the prior optical assemblies, and/or d) a cooling medium such as air was actively used to flow over or through the optical assemblies to control their temperature. Options b) and c) are not available to use in the EUV tool because EUV light does not sufficiently penetrate a pellicle.

An additional challenge to an actinic EUV reticle inspection tool that uses a time delay integration (TDI) assembly is that TDI sensors and their associated electronics dissipate a significant amount of heat. In atmospheric pressure tools (e.g., every existing reticle inspection tool), that heat is transferred to air to avoid heating nearby optics. This transfer of heat to air is not possible in an EUV tool since they operate in a vacuum. Therefore, the heat will generally be transferred to a water-cooled coldplate, whose operating temperature is selectable since the TDI operation is not strongly dependent upon its own temperature. There is a range of temperatures created near each TDI as each is cooled. The midpoint of that range is selectable by varying the cooling liquid temperature. However, many of those temperature zones have a view factor to the optics assembly components and thus will potentially transfer heat to or from those components.

Thermal control of the TDI in prior tools was done with air blowing across the back of the TDI package and across electronics associated with the TDI. The air performing this cooling function was supplied from the room in which the tool is located or from exhaust from other cooled portions of the tool. Exact control of the temperature of the TDI was not required. Prior methods have only been used to ensure that the TDI temperature did not exceed some threshold that would compromise the performance of the TDI, or to limit the heating of nearby elements to some nominal change (e.g., ±0.5° C.). The control was not intended to limit the actual heat transfer, merely the gross temperature changes of nearby elements.

Accordingly, it would be advantageous to develop effective methods and apparatus to minimize thermal impact to reticle and optical assemblies that overcome these shortcomings. It is within this context that embodiments of the present invention arise.

SUMMARY OF THE INVENTION

Aspects of the present disclosure describe an optics assembly configured to focus light from an EUV source onto a reticle and then direct that light onward to a sensor. A plate with an opening allows the EUV light to pass through is disposed between the optics assembly and the reticle, wherein the plate is cooled to a temperature less than that of the reticle or sensor. Also, the plate is engineered to balance out radiant heat from the reticle or sensor with heat absorbed by the plate.

According to an additional aspect of the present disclosure a portion of the plate that has a view to the optics assembly has been engineered to have an emissivity that is different from other portions of the plate.

Aspects of the present disclosure also describe a sensor assembly with a water-cooled cold plate wherein the plate is cooled to a temperature sufficient to balance out heat transfer from the sensors with heat from the optics assembly absorbed by the cold plate.

According to an additional aspect of the present disclosure a portion of the cold plate that has a view to the optics assembly has been engineered to have an emissivity that is different from other portions of the cold plate.

BRIEF DESCRIPTION OF THE DRAWINGS

Objects and advantages of the invention will become apparent upon reading the following detailed description and upon reference to the accompanying drawings in which.

DESCRIPTION OF THE SPECIFIC EMBODIMENTS

Figure 1:
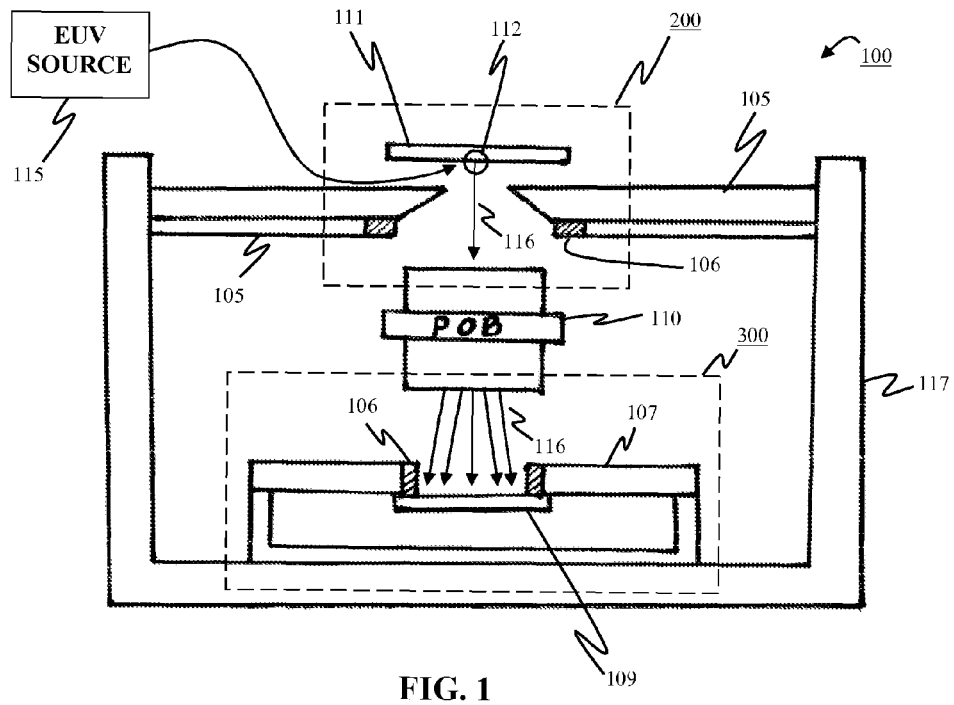
FIG. 1 is a cross-sectional diagram of an inspection tool according to certain aspects of the present disclosure.

Although the following detailed description contains many specific details for the purposes of illustration, anyone of ordinary skill in the art will appreciate that many variations and alterations to the following details are within the scope of the invention. Accordingly, the exemplary embodiments of the invention described below are set forth without any loss of generality to, and without imposing limitations upon, the claimed invention. Additionally, because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention.

INTRODUCTION

Several particle protection mechanisms have been proposed, studied, and/or used. One such device is called a thermophoretic plate. One incarnation of that hardware is placing a cooled plate near the face of the reticle. The plate has a hole in its center to allow the EUV light to strike the reticle face and be reflected back to the imaging optics. In general, this cooled plate will be lower in temperature than any nearby hardware.

Furthermore, thermophoresis is only an effective particle protection strategy in low-pressure regimes, in which prior reticle inspection tools have not been. In tools where EUV reticles have been protected using thermophoretic plates, temperature control has been done using cooled electrostatic chucks so the small amount of temperature change from the radiation to the thermophoretic plate could be ignored.

Controlling the temperature of a reticle in a low-pressure EUV tool has been done in the past primarily via a water-cooled electrostatic chuck. These devices have direct contact with the back of the reticle and can create many particles. To keep the reticle as stable dimensionally as possible during an inspection, its temperature should be kept as stable as possible. In general, one of the implications of this is to surround the reticle with surfaces whose temperatures match that of the reticle as closely as possible. However, a thermophoretic plate works by having a temperature significantly lower than the reticle surface.

Aspects of the present disclosure are directed at reducing the heat load into the EUV projection optics box (POB), and thus will make the optics within the POB more stable and less likely to exhibit a difference between the as-delivered optics and the in-use optics. In order to ensure that the heat load on the POB is zero or very close to zero, the heat flux of the components in the EUV system that are at a different temperature than the POB must be analyzed. Preferably, the net heat flux seen by the POB should be zero.

According to a first aspect of the present disclosure, the heated portion of the reticle and the thermophoretic plate are engineered to have a net heat flux seen by the POB of zero. Both the hot spot and some portion of the cooled thermophoretic plate will have a view factor to the optic assemblies. By itself, the hot spot will radiate heat into the optical assemblies. By itself, the thermophoretic plate will remove heat from the optical assemblies. By adjusting the size, exposed area, emissivity, or temperature of the thermophoretic plate, a near zero total heat load to the optical assemblies can be achieved.

FIG. 1 is a cross-sectional diagram of an EUV inspection tool 100 according to an aspect of the present disclosure. An EUV source 115 produces EUV light 116 that is directed to a focus point 112 on a reticle 111. The EUV source 115 may be inside or outside of an enclosure 117. By way of example, the enclosure 117 may be a vacuum chamber or other low pressure chamber suitable for use with EUV tools. The reticle 111 may be moved, but the location of the point 112 remains constant. This enables various locations on the reticle 111 to be analyzed. However, the EUV light focused at that point may cause a substantial increase in the temperature of the reticle 111 at the focus point 112. By way of example, and not by way of limitation, the temperature of the reticle 111 at the focus point 112 may be increased to approximately 100° C.

The EUV light 116 that is reflected off of the reticle 112 then passes through an opening in a thermophoretic plate 105 before entering into the projection optics box (POB) 110. The thermophoretic plate 105 may have engineered emissivity portions 106 on portions of the plate that have view of the POB 110. The engineered emissivity portions 106 may include a surface coating and/or a surface treatment on portions that have a different emissivity than that of the material used for the thermophoretic plate 112. By way of example, and not by way of limitation, the surface treatment may comprise a nickel coating over the thermophoretic plate 105 that has a surface etched with nitric acid. Additionally, the thermophoretic plate 105 may be liquid cooled. As such, it is possible to control the temperature of the thermophoretic plate 105. Further, the thermophoretic plate 105 may have separate zones where each zone of the plate may be maintained at a separate temperature.

The EUV light 116 exits the POB 110 and interacts with a sensor 109. By way of example, and not by way of limitation, the sensor 109 may be a single sensor, or an array of sensors. By way of example, and not by way of limitation, the sensors may be time delay integration (TDI) sensors, or charge-coupled device (CCD) sensors. A cold plate 107 may be placed above the sensor 109. By way of example, the cold plate 107 may be water cooled. Therefore, the cold plate 107 may have a controllable temperature. Further, portions of the cold plate may further include engineered emissivity portions 106. The engineered emissivity portions 106 used on the cold plate 107 may be substantially similar to those used on the thermophoretic plate 105. The engineered emissivity portions 106 may be formed on portions of the cold plate that have a view-factor that includes a portion of the POB 110. As shown in FIG. 1, only the through hole in the plate where the EUV light 116 passes through is an engineered emissivity portion. However, the top surfaces of the cold plate may also be engineered emissivity portions 106.

The amount of surface area of the cold plate 107 or the thermophoretic plate 105 that is an engineered emissivity portion 106 does not affect the bulk properties of either component. Since the engineered emissivity portions 106 are merely surface treatments or coatings, the thermal and electrical properties of the bulk are substantially similar.

Figure 2:
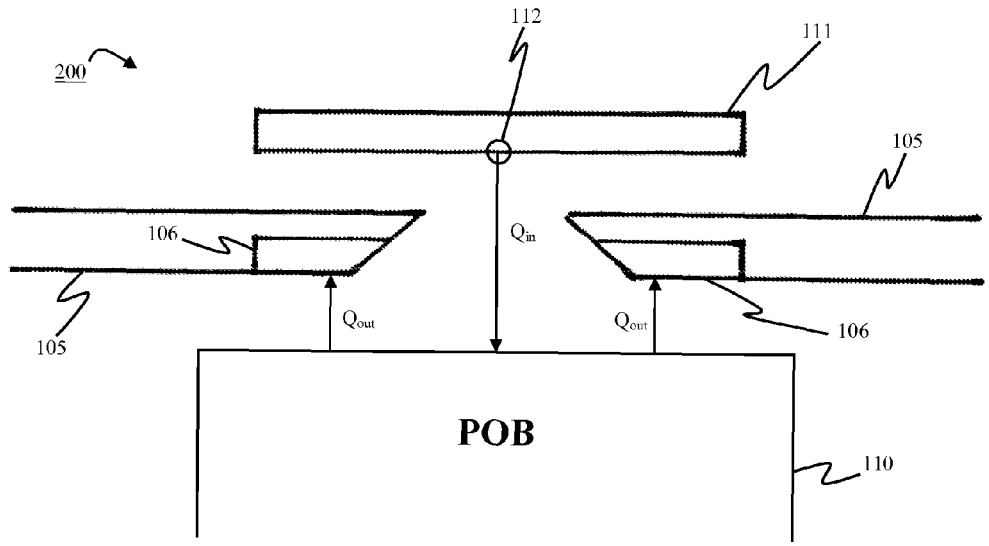
FIG. 2 is a zoomed in view of a thermophoretic plate portion of the inspection tool according to certain aspects of the present disclosure.

FIG. 2 is a zoomed in view of box 200 from FIG. 1. FIG. 2 shows the reticle 111 focus position 112, the thermophoretic plate 112 with engineered emissivity portions 106, and a top portion of the POB 110. In FIG. 2 the arrows represent the radiated heat Q between the components. The major component of heat $Q_{in}$ radiated into the POB 110 seen in this figure is from the focus position 112 on the reticle 111. Typically, the POB 110 may be maintained at a temperature around 22° C.

Since the focus position 112 may reach temperatures of approximately 100° C. the radiation of heat from the focus position 112 to the POB 110 may be significant. Therefore, in order to prevent a change in temperature of the POB 110 that may degrade its optical performance, the thermophoretic plate may be maintained at a temperature below that of the POB and designed to have improved emissivity in order to absorb radiated energy from the POB 110. In order to ensure that the temperature of the POB 110 does not change portions of the thermophoretic plate may be engineered emissivity portions 106. The size and emissivity of the engineered emissivity portions 106 should be chosen such that the heat $Q_{out}$ radiated from the POB 110 to the thermophoretic plate 105 balances the amount of heat radiated from the focus position 112 to the POB 110.

The amount of heat that needs to be absorbed by the thermophoretic plate 105 may be determined in several ways. First, since the energy of the EUV light 116 and the temperature of the POB are known, the amount of heat transferred between them (both by radiation and gas conduction) may be calculated. The thermophoretic plate may then be engineered such that the combination of its emissivity and temperature control result in an equal amount of heat transferring from the POB 110 to the thermophoretic plate 105. Alternatively, a dynamic measurement system may be used as well. For example, a temperature reading may be taken of the POB 110. When the temperature of the POB changes such that it is outside of a specified tolerance above a certain threshold, the temperature of the thermophoretic plate 115 may be changed. By way of example, this may be implemented with a feedback loop.

Figure 3:
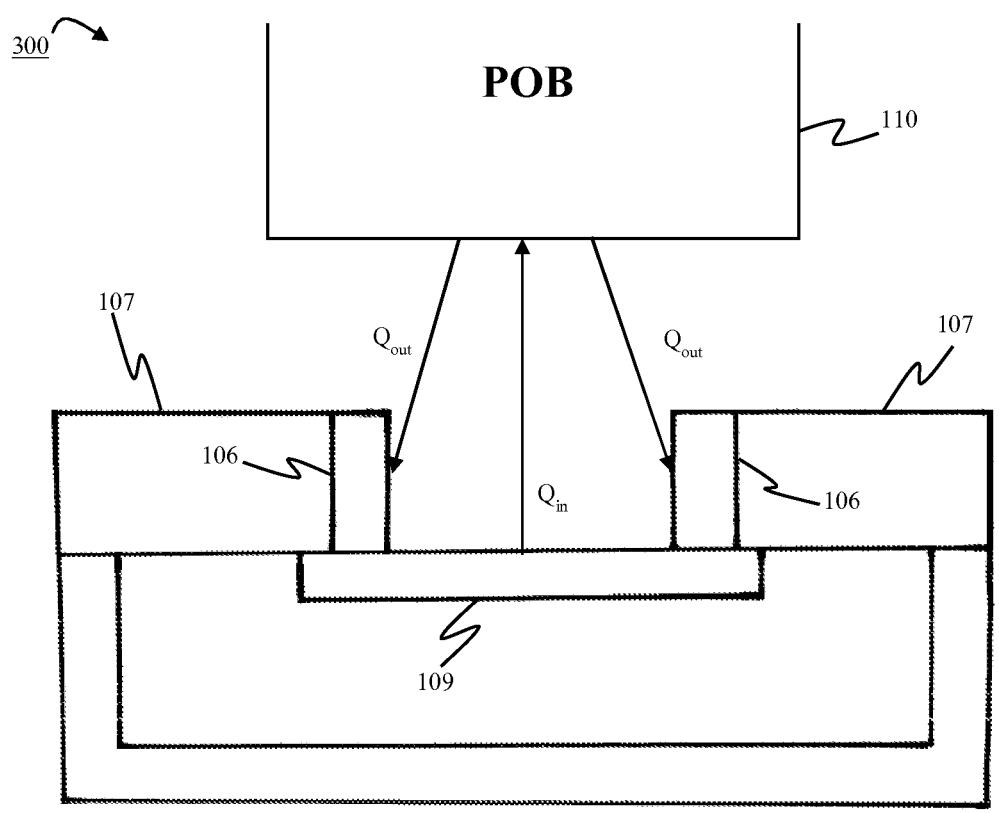
FIG. 3 is a zoomed in view of a TDI array portion of the inspection tool according to certain aspects of the present disclosure.

FIG. 3 is a zoomed in view of box 300 from FIG. 1. FIG. 3 shows the sensor 109, the cold plate 107 with engineered emissivity portions 106 and a lower portion of the POB 110. In FIG. 3, the arrows represent the radiated and conducted heat between the components. The major component of heat $Q_{in}$ radiated into the POB 110 seen in this figure is from the sensor 109. The sensor may reach temperatures of approximately 40° C. and therefore may radiate and conduct heat to the POB 110. Further, as the number or size of the sensors 109 increases the effect becomes even larger. Therefore, in order to prevent a change in temperature of the POB 110 that may degrade its optical performance, the cold plate 107 may be maintained at a temperature below that of the POB and be engineered to have improved emissivity in order to absorb radiated energy from the POB 110. The size and emissivity of the engineered emissivity portions 106 should be chosen such that the heat $Q_{out}$ transferred from the POB 110 to the cold plate 107 balances the amount of heat transferred from the sensor 109 to the POB 110. The amount of heat that needs to be absorbed by the cold plate may be determined in substantially the same manner as that used for the thermophoretic plate 105. By way of example, the heat produced by the sensor is known, and therefore, the amount of heat that is transferred into the POB 110 may be calculated. With this information, the size of the engineered emissivity portions 106 and the temperature at which the cold plate is maintained may be calculated in order to balance the radiated heat into the POB 110. Additionally, the amount of heat transferred from the POB 110 to the cold plate 107 may be altered dynamically by monitoring the temperature changes and adjusting the temperature of the cold plate.

According to an additional aspect of the present disclosure, the heat from the POB 110 may be removed with thermoelectric cooling. This may be desirable since EUV tools often operate in low pressure or vacuum conditions, and therefore transferring heat through convection is not feasible. Thermoelectric cooling of the POB 110 may use the Peltier effect to create a heat flux between the POB 110 and the thermophoretic plate 105 and/or the cold plate 107. A Peltier cooler may then transfer heat from the POB 110 to the thermophoretic plate 105. Since the thermophoretic plate and cooling plate are held at a low temperature (e.g., water cooling) the heat may be dissipated.

According to additional aspects of the present disclosure, a thermally controlled plate with engineered emissivity and/or temperature portions 106 may be utilized in any type of tool that utilizes EUV processes. For example, an EUV lithography tool will also have temperature sensitive optics that may be exposed to excess heat. Since the EUV processing is done in a vacuum, traditional convection heat transfer is not possible. Therefore, it is desirable to have controlled emissivity portions 106 on components that are below the temperature of the optics that may be used to enhance the radiation of heat from the optics to the cooled component.

Figure 4:
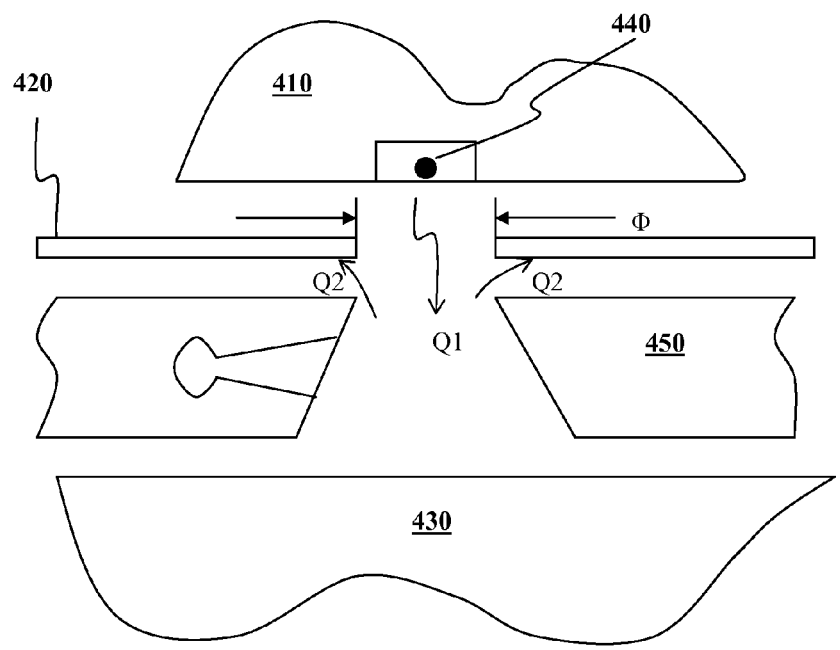
FIG. 4 is a cross-sectional view of an inspection tool according to an aspect of the present disclosure.

The method according to the present disclosure utilizes the newly existing elements whose temperatures differ from the assemblies to be used in concert to balance the radiative and gas conducted heat loads. As illustrated in FIG. 4, a thermophoretic plate 420, as large as or larger than the reticle 410, is thermally isolated from nearby hardware. The temperature of the plate 420 is controlled actively to be 5-15° C. below the temperature of the reticle 410. The temperature of the reticle 410 will probably be controlled to be the same as the optical assembly 430. The arrows for Q represent the heat transferred between the components. The thermophoretic plate 420 works in the presence of a low-pressure gas within the system to preferentially push particles toward the thermophoretic plate 420 and away from the reticle 410. A small amount of the thermophoretic plate 420 will have a view factor to the optics and will be drawing heat Q2 from the optics via radiation and conduction. The heated spot 440 on the reticle 410 will be supplying heat Q1 to the optics, also via radiation and gas conduction. By choosing the visible area and temperature of the thermophoretic plate 420, the heat load on the optics can be designed to be very nearly zero. Using the method described herein can significantly reduce the amount of heat transferred to the reticle-side of the illumination and imaging optics. This concept for temperature control can work in the absence of large volumes of flowing air, in vacuum, and with optical systems exhibiting high thermal sensitivity.

Alternatively, the size of the central hole in the thermophoretic plate may be driven by particle management concerns, and may thus not be a variable that can be changed for thermal control purposes. Rather than changing the size of the central hole in the thermophoretic plate, one could achieve a similar result by changing the surface properties of the portion of the plate that faces the reticle. This could be used to change the emissivity of the plate and thus the amount of heat transfer. Another possible method of changing the heat radiated between the thermophoretic plate and the optics is to place a radiation baffle of a controlled size and material in between the two items. In some implementations, the radiation baffle may have other functions.

Figure 5:
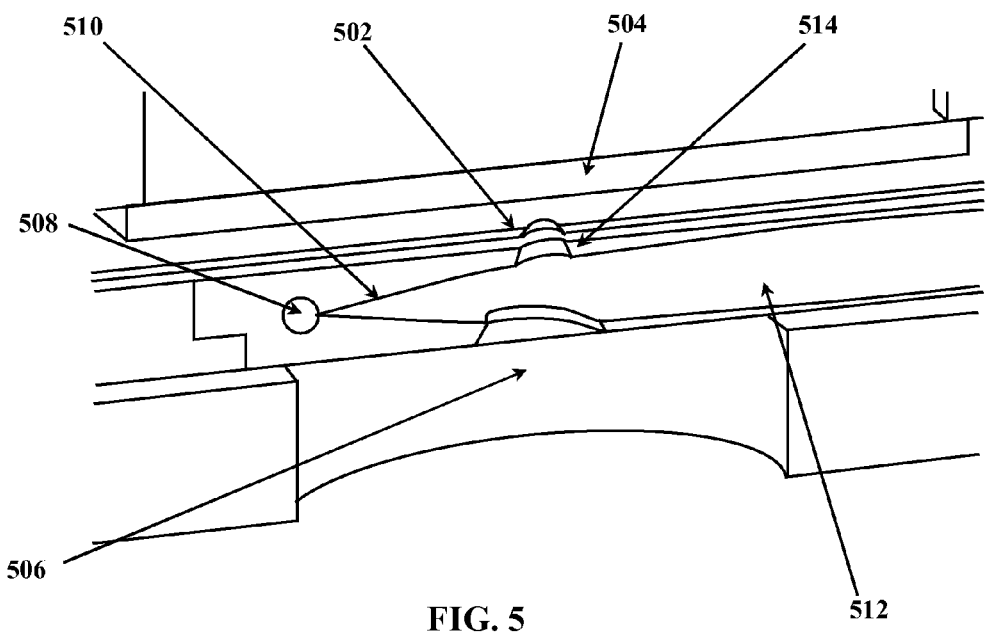
FIG. 5 is a CAD model of one exemplary inspection tool according to an aspect of the present disclosure.

By way of example, and not by way of limitation, the radiation baffle may take the form of the particle protection gas nozzle assembly 500 in the design possibility shown in FIG. 5. In this example a thermophoretic plate 502 with an aperture may be located between an EUV reticle 504 and a structure configured to provide gas flow across an optical path 506. The structure may include a gas reservoir 508 in communication with an exhaust duct 510 via a laval nozzle 512. The reservoir 508, nozzle 510, and exhaust duct 512 are configured to provide a flow of gas across an aperture 514 that lies along the optical path 506.

Another aspect of the present disclosure is to minimize the thermal impact to the reticle. Research has shown that, for a thermophoretic plate to be effective, a temperature gradient of at least 10° C./cm of distance between the reticle and the thermophoretic plate must be maintained. The greater the distance, the greater the dT (temperature difference) must be between the two surfaces. The amount of heat transferred via radiation and gas conduction between two parallel plates in close proximity is driven primarily by the emissivity of the two surfaces and the dT between them. A low-emissivity coating, e.g., nickel or polished gold, will reduce the radiation heat transfer but will not alter the thermophoretic effect on the gas molecules.

Figure 6:
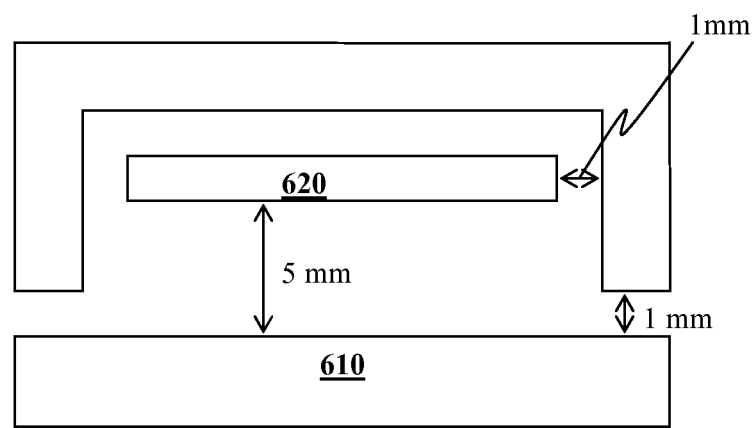
FIG. 6 is an additional cross sectional view of an inspection tool according to an aspect of the present disclosure.

Reducing the heat load into the reticle in accordance with aspects of the present disclosure can improve the stability and reducing the unwanted mechanical distortion of the reticle during an inspection. As illustrated in FIG. 6, these goals may be achieved by placing the thermophoretic plate near the reticle 620 (thus reducing required dT and its associated unwanted radiation) and with the use of low-emissivity materials or coatings on the surface of the thermophoretic plate 610 to reduce the radiation directly. For example, FIG. 6 shows a possible implementation within an actinic EUV reticle inspection tool. In this example, the implementation takes the form of a 5° C. cooler-than-the-reticle, gold-plated thermophoretic plate 5 mm away from the inspected surface rather than a 10° C. cooler-than-the-reticle, bare aluminum thermophoretic plate 10 mm away from the inspected surface. In one example, the temperature of the reticle 620 is 22° C. and the temperature of the plate 610 is 17° C. By keeping the gap between the thermophoretic plate and the reticle as small as possible, the dT may be minimized. Minimizing dT reduces the heat transfer between the thermophoretic plate and the reticle. By way of example, the distance between the reticle and the plate may be about 5 millimeters. Further, by ensuring that the top surface of the thermophoretic plate has a low emissivity, the radiative heat transfer can be reduced without compromising the thermophoretic effect, which relies on gas molecules physically touching the thermophoretic plate to change their temperature. This simple concept does not weaken the thermophoretic effect that helps protect the reticle from particles in any way but it does significantly reduce the unwanted temperature effects of having a cooled plate exposed directly to the reticle.

In addition, reducing heat load as discussed herein does not require an electrostatic chuck, although it can work with one. Alternatively, variables of emissivity and distance from the inspected surface may be varied to achieve the desired performance. In addition, the temperature profile of the thermophoretic plate does not need to be uniform and gradients around and along the plate could be used to further reduce thermal effects.

Figure 7:
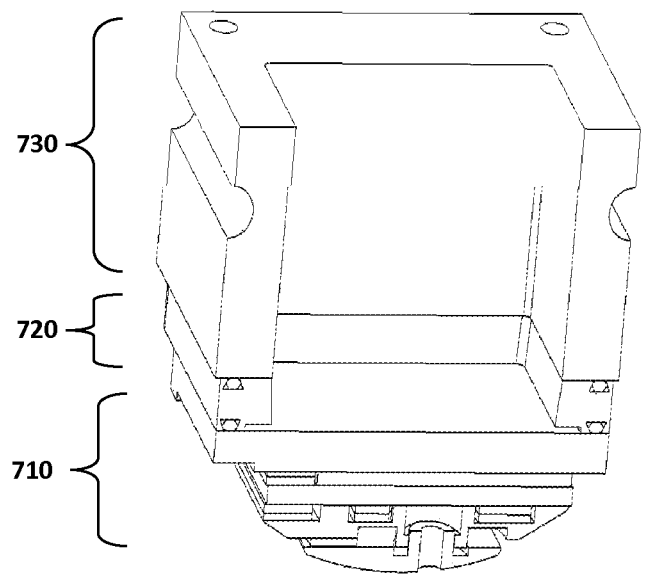
FIG. 7 depicts temperature distribution in the vicinity of the TDI on its cool mount according to an aspect of the present disclosure.

Yet another aspect of the present disclosure is to minimize thermal impact of TDI sensors in EUV inspection tool using TDI assembly. Selecting a cooling liquid temperature so the transfer of heat, in general or to a specified location, can be set to zero. In addition, on those elements whose materials and/or coatings can be controlled, the emissivity of those items may be chosen to aid in balancing out the net flow of heat to the optics or to the housing surrounding the optics. This new method utilizes the plate which will contain the multiple (currently 14) TDI packages. This plate may be cooled using a liquid coolant since the total power dissipated in the TDI assembly is over 500 W and there is no air available to remove the heat. FIG. 7 shows the temperature distribution in the vicinity of the TDI on its cool mount. The distribution and rate of that coolant flow and the inlet temperature of that coolant may be controlled. In one example, the temperature distribution for zone 710 is ranging from about 21.77 to about 37.14. The temperature distribution for zone 720 is ranging from about 8.589 to about 10.79. For zone 730, the temperature distribution is about 2.00. The nominal inlet temperature may be set such that the total heat flow from the TDI assembly to the optics assembly (or a prescribed portion of the optics assembly) is nominally zero. This balancing can be made easier with the allowable use of various coatings on some TDI assembly surfaces. Such coatings can be configured to selectively reduce or increase the nominal radiative coupling. This concept for temperature control can work in the absence of large volumes of flowing air, in vacuum, and with optical systems exhibiting high thermal sensitivity. An alternate method to balance out the heat between the TDI assembly and the optics assembly is to allow the TDI assembly to achieve some arbitrary temperature above the optics assembly, transmitting heat to the optics assembly. Then, a separately cooled plate or plates of a known size and emissivity draw an equivalent amount of heat from the optics assembly.

Figure 8:
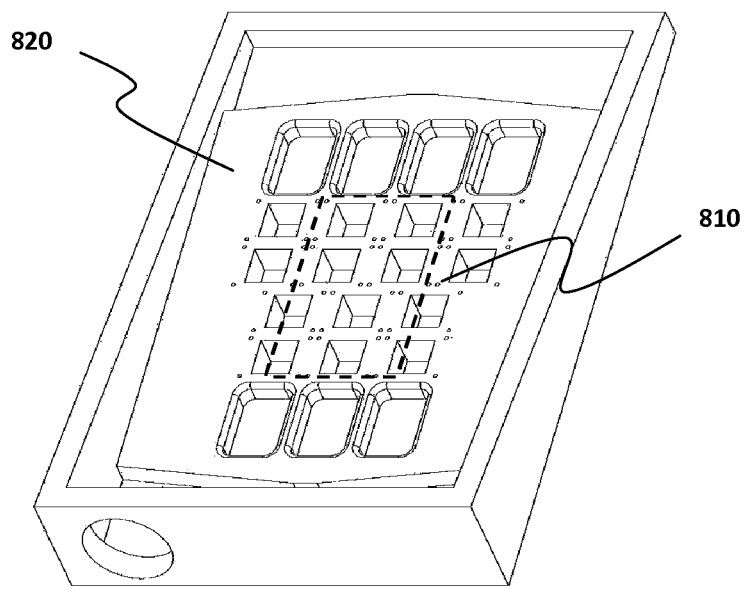
FIG. 8 depicts a TDI assembly plate used in an inspection tool according to an aspect of the present disclosure.

By way of example, and not by way of limitation, in one implementation an array of 14 TDI sensors face a temperature-sensitive set of optics. The TDI sensors, which dissipate a significant amount of heat, are mounted to a cold plate that is cooled with a liquid whose temperature may be freely selected. With proper selection of the coolant temperature, the heat transferred to the optics assembly may be adjusted to approximately zero. FIG. 8 depicts a TDI assembly plate that has a view factor to the optics assembly within the actinic EUV reticle inspection tool in accordance with an aspect of the present disclosure. The cooling liquid is brought into the TDI cooling plate at below 0° C., and the surfaces that face the optics assembly range from a few degrees below the optics temperature to a few degrees above the optics temperature. Respectively, these surfaces absorb heat from, or transmit heat to, the optics assembly. Specifically, the surface area 810 on the TDI assembly plate is at a higher temperature than the temperature of the optics assembly and thus radiate heat into the optics assembly. However, the surface area 820 surrounding the TDI assembly is cooler than the optics assembly and thus pulls heat from the optics assembly. With proper balancing of temperatures, view factors, and material coatings, the two effects can be made to cancel one another, resulting in nearly zero net heat transfer. This invention can reduce the heat load into the EUV inspection system optics, and thus will make them more stable and less likely to exhibit a difference between the as-delivered optics and the in-use optics.

In this document, the terms "a" and "an" are used, as is common in patent documents, to include one or more than one. In this document, the term "or" is used to refer to a nonexclusive "or," such that "A or B" includes "A but not B," "B but not A," and "A and B," unless otherwise indicated. The following detailed description, therefore, is not to be taken in a limiting sense, and the scope of the present invention is defined by the appended claims. "Optional" or "optionally" means that the subsequent described circumstance may or may not occur, so that the description includes instances where the circumstance occurs and instances where it does not. For example, if a device optionally contains a feature A, this means that the feature A may or may not be present, and thus, the description includes both structures wherein a device possesses the feature A and structures wherein the feature A is not present.

The appended claims are not to be interpreted as including means-plus-function limitations, unless such a limitation is explicitly recited in a given claim using the phrase "means for." Any element in a claim that does not explicitly state "means for" performing a specified function, is not to be interpreted as a "means" or "step" clause as specified in 35 USC §112, ¶6. In particular, the use of "step of" in the claims herein is not intended to invoke the provisions of 35 USC §112, ¶6.

What is claimed is:

1. An apparatus comprising:
   an optics assembly configured to direct light from an EUV source onto a workpiece, wherein the optics assembly is maintained at a specific temperature; and
   a plate with an opening to allow the EUV light to pass through disposed between the optics assembly and the workpiece, wherein the plate is cooled to a temperature less than the specific temperature and wherein the plate is engineered to balance out heat radiated from the workpiece with heat absorbed by the plate when the EUV light impinges on the workpiece, wherein a portion of an area of the plate that has a view to the optics assembly and is less than a full area of the plate is engineered to have an emissivity that is different from other portions of the area of the plate.

2. The apparatus of claim 1, wherein the portion of the plate that has a view to the optics assembly has a surface treatment or a surface coating to have an emissivity different from other portions of the plate, the surface treatment or the surface coating comprising a nickel coating.

3. The apparatus of claim 1, wherein the plate is cooled by using a liquid coolant.

4. The apparatus of claim 1, wherein the workpiece includes at least one TDI sensor or at least one CCD sensor.

5. The apparatus of claim 1, wherein the plate is disposed near the workpiece in a distance of about 5 millimeters.

6. The apparatus of claim 1, wherein the plate has a surface facing the workpiece, the surface having a low emissivity.

7. The apparatus of claim 6, wherein the surface is gold-plated.

8. The apparatus of claim 1, further comprising a radiation baffle disposed between the plate and the optics assembly.

9. The apparatus of claim 1, wherein the plate has separate zones, each of the zones being maintained at a separate temperature.

10. A method, comprising:
    directing light by an optics assembly from an EUV source onto a workpiece, wherein the optics assembly is maintained at a specific temperature;
    passing the EUV light through a plate with an opening, wherein the plate is disposed between the optics assembly and the workpiece and wherein the plate is cooled to a temperature less than the specific temperature;
    balancing out radiant heat from the workpiece with heat absorbed by the plate when the EUV light impinges on the workpiece, wherein a portion of an area of the plate that has a view to the optics assembly and is less than a full area of the plate is engineered to have an emissivity that is different from other portions of the area of the plate.

11. The method of claim 10, wherein the portion of the plate that has a view to the optics assembly has a surface treatment or a surface coating to have an emissivity different from other portions of the plate, the surface treatment or the surface coating comprising a nickel coating.

12. The method of claim 10, wherein the plate is cooled by using a liquid coolant.

13. The method of claim 10, wherein the workpiece includes at least one TDI sensor or at least one CCD sensor.

14. The method of claim 10, wherein the plate is disposed near the workpiece in a distance of about 5 millimeters.

15. The method of claim 10, wherein the plate has a surface facing the workpiece, the surface having a low emissivity.

16. The method of claim 15, wherein the surface is gold-plated.

17. The method of claim 10, further comprising a radiation baffle disposed between the plate and the optics assembly.

18. The method of claim 10, wherein the plate has separate zones, each of the zones being maintained at a separate temperature.

19. The apparatus of claim 1, wherein the workpiece is a reticle or a sensor wafer.

20. The apparatus of claim 1, wherein the plate is cooled to a temperature about 5-15° C. less than the specific temperature.

* * * * *